United States Patent [19]

Frey et al.

[11] Patent Number: 5,681,657
[45] Date of Patent: Oct. 28, 1997

[54] BIOCOMPATIBLE POROUS HOLLOW FIBER AND METHOD OF MANUFACTURE AND USE THEREOF

[75] Inventors: Rainer H. Frey, Watzmannstrasse 10, D-82319 Starnberg; Lothar Sellin, Keltenstrasse 35, D-52074 Aachen, both of Germany

[73] Assignees: Rainer H. Frey, Starnberg; Lothar Sellin, Aachen; H. Peter Brehm, Starnberg, all of Germany

[21] Appl. No.: 596,389

[22] Filed: Jan. 31, 1996

[30] Foreign Application Priority Data

Feb. 2, 1995 [DE] Germany ............... 195 03 391.4
May 15, 1995 [DE] Germany ............... 195 17 754.1

[51] Int. Cl.⁶ .................................................. D02G 3/00
[52] U.S. Cl. ...................... 428/375; 482/398; 482/400
[58] Field of Search ........................ 427/244, 412.3; 428/368, 375, 376, 398, 400

[56] References Cited

U.S. PATENT DOCUMENTS

| | | | |
|---|---|---|---|
| 3,276,448 | 10/1966 | Kronenthal et al. | 128/334 |
| 3,526,005 | 9/1970 | Bokros . | |
| 3,685,059 | 8/1972 | Bokros et al. | 128/1 R |
| 3,952,334 | 4/1976 | Bokros et al. | 128/92 C |
| 4,164,045 | 8/1979 | Bokros et al. | 128/334 |
| 4,204,542 | 5/1980 | Bokros et al. | 128/335.5 |
| 4,457,984 | 7/1984 | Otani et al. | 428/220 |
| 4,690,763 | 9/1987 | Zieger et al. | 210/510.1 |
| 4,699,681 | 10/1987 | Kasmark, Jr. et al. | 55/316 |
| 4,718,907 | 1/1988 | Karuoski et al. | 623/12 |
| 4,808,315 | 2/1989 | Manabe et al. | 210/645 |
| 4,816,332 | 3/1989 | Fujita et al. | 427/244 |
| 5,104,425 | 4/1992 | Rao et al. | 55/16 |
| 5,124,177 | 6/1992 | Kasmark, Jr. et al. | 427/244 |
| 5,336,164 | 8/1994 | Snider et al. | 604/4 |
| 5,370,684 | 12/1994 | Vallana et al. | 623/1 |
| 5,435,836 | 7/1995 | Anand et al. | 95/45 |
| 5,543,218 | 8/1996 | Bennett et al. | 428/375 |

FOREIGN PATENT DOCUMENTS 1 226 833    3/1971    United Kingdom .

OTHER PUBLICATIONS

World Patent Index, Referral-No. 08781 D/06 TOYJ 24 May 1979.
World Patent Index, Referral-No. 69927 A/39 HITM 4, Feb. 1977.
Müller et al., German Language Survey Article (1986), vol. 57, pp. 64-71, concerning Vascular Prostheses.

*Primary Examiner*—Newton Edwards
*Attorney, Agent, or Firm*—Pollock, Vande Sande & Priddy

[57] ABSTRACT

A biocompatible porous hollow fiber made of a polyolefin material and having a coating of biocompatible carbon material wherein the coating is obtained by a process comprising the following steps:

introducing a preformed porous hollow fiber into an atmosphere of gaseous monomer vinylidene chloride (1,1 di-chloro ethylene);

inducing a graft-polymerization reaction and grafting a uniform layer of polyvinylidene chloride on the polyolefin material forming the porous hollow fiber; and substantially eliminating and removing hydrogen chloride (dehydrochlorination reaction) from the polyvinylidene chloride in order to convert the polyvinylidene chloride layer into a coating of biocompatible carbon material.

23 Claims, 5 Drawing Sheets

× Hollow fiber comprising 30% porosity subsequently to the grafting reaction
△ Hollow fiber comprising 30% porosity subsequently to the dehydrochlorination reaction
* Hollow fiber comprising 40% porosity subsequently to the grafting reaction
□ Hollow fiber comprising 40% porosity subsequently to the dehydrochlorination reaction

BIOCOMPATIBLE POROUS HOLLOW FIBER AND METHOD OF MANUFACTURE AND USE THEREOF

TECHNICAL FIELD

The present invention relates to a biocompatible porous hollow fiber made of a polyolefin material and having a coating of a biocompatible carbon material. In the present context "biocompatible" means especially excellent compatibility with respect to blood and tissue; in particular biocompatibility includes haemocompatibility and thromboresistance. The biocompatible porous hollow fiber according to the present invention is especially suited for providing exchange materials, diaphragmas and/or semipermeable membranes within devices, which will contact blood or plasma outside the living body, such as in oxygenators, haemo concentrators, dialyzer apparatuses, haemo filter devices and the like, and for providing surfaces which will contact blood and/or plasma and in other equipments for maintaining an extracorporal circulation of blood and/or plasma.

BACKGROUND ART

Further, the present invention relates to a method of manufacturing the biocompatible porous hollow fiber.

Moreover, the present invention relates to specific kinds of use of the biocompatible porous hollow fiber, especially for providing exchange materials, diaphragmas and/or semipermeable membranes in oxygenators, dialyzer apparatuses, haemo concentrators, haemo filters and other components of an extracorporal blood circulation.

Microporous open-celled hollow fibers are well known in the art. An especially important application concerns the use as exchange materials or as intermediate product for providing exchange materials, diaphragmas and/or semipermeable membranes for effecting a gas exchange, for example in oxygenators, for purposes of filtration, ultra-filtration and micro-filtration, for example in blood filter devices, in dialyzer apparatuses, for effecting a reverse osmosis, for effecting a heat exchange and the like. A degree of porosity and the number, form and dimensions of pores will be matched to the specific kind of use. Typically, the porosity may range of from 10 to 50 %, and the pores may comprise a dimension, especially a diameter less than one micron. In these fields of use, the hollow fiber wall will typically contact blood and/or plasma. Commonly used hollow fiber materials include polyester, polyethylene and especially polypropylene.

In general, two different methods are available for preparing microporous open-celled hollow fibers consisting of polypropylene. According to a first alternative, non-drawn hollow fibers will be substantially drawn at a temperature lower than 110° C. This kind of drawing provides porous areas being oriented vertically to the drawing direction. A method of this type is disclosed in German patent specification No. 26 30 374. According to a further proposal of this kind, a hot-drawing step may be effected subsequently to the cold-drawing step, as disclosed in German Offenlegungsschrift No. 30 03 400. According to another, second alternative, a homogenous one-phase mixture is provided comprising a fiber-forming polymer such as polypropylene and further comprising an additional liquid phase being inert with respect to the fiber-forming polymer. This two-component mixture is extruded into a bath, wherein the formed hollow fiber will solidify. Thereafter, the hollow fiber is treated with a solvent in order to dissolve and remove the liquid phase.

This removal of the liquid phase generates pores and micropores within the hollow fiber wall. This method is disclosed in German patent specification No. 28 33 493. According to a modified version of this method, microporous hollow fibers may be obtained which consist of polyethylene, as disclosed in German patent specification No. 27 18 155.

In the present context "biocompatible" or "biocompatibility" describes the mutual effects of the polymer fiber material with blood and/or plasma. Natural active blood forms a living system of cells, factors and proteins which act rather aggressively upon foreign surfaces. A contact of blood with such foreign surfaces may cause a haemolysis which decreases the number of active erythrocytes yielding in a reduced capacity of oxygen take-off and oxygen transportation. In order to overcome this defect, a higher oxygen partial pressure has to be provided within an extracorporal circulation system, which may enhance the haemolysis. Further, leukocytes may be deposited on the fiber surface; subsequently to an operation, those deposited leukocytes are missing, and the decreased number of leukocytes in the blood of a patient increases the danger of post-operative infection.

Further, the fiber surface may activate the so called complement complex which effects the immuno system and the blood factors. Finally, the fiber surface may activate the blood coagulation cascade including a fibrinogenesis until the formation and deposition of fibrin clots and thrombi. Therefore, the fiber surface shall comprise a biocompatibility as high as possible in order to inhibit or completely hinder an activation of the fore-mentioned processes. Especially, the fiber surface shall comprise a high haemo compatibility and a low tendency for thrombus forming (anti-thrombogenity).

Among the actually available biocompatible materials, pyrolytic carbon seems to be one of the materials having the best biocompatible characteristics. Typically, the pyrolysis of carbon containing starting materials and depositing the so formed particulate pyrolytic carbon on a substrate requires high temperatures in the range of from 800° to 1000° C. and higher. Medical prosthetic devices comprising a coating of pyrolytic carbon and methods of manufacture are disclosed in the U.S. Pat. Nos. 4,164,045 or 3,952,334 or 3,685,059 or 3,526,005. The common substrate materials, especially materials based on organic polymers, will be irreversibly impaired by such high temperatures. The European Patent Specification EP 0 224 080 B1 and the U.S. Pat. No. 5,370,684 disclose a method of manufacture a prosthetic device, comprising a substrate made of an organic polymer ("DACRON", "TEFLON") and having a coating of biocompatible carbon material. For example, a coated DACRON yarn is described in said patent which may be used as suture yarn. The coating has been deposited on said yarn at relatively low temperatures by sputtering a carbon target at a given voltage and current. The thus obtained coating has a thickness less than 1.0 micron. The thus obtained carbon material is said to consist of turbostratic carbon. The known method is complex and expensive and provides a relatively low productivity.

In case of an improper contact, the extremely thin carbon layer may easily be stripped off from the yarn or from other substrates.

Typically, oxygenators, dialyzers, blood filters, haemo concentrators and similar devices are intended and designed for a one-time use. Typically those devices comprise more than 1 m² exchange surface which is based on porous hollow fibers. Therefore, porous hollow fibers of this kind are required and used in large quantities. The fore-mentioned low temperature sputtering process is too expensive in order to coat large quantities of hollow fibers with pyrolytic or turbostratic carbon according to this process.

According to other proposals, for example British Patents 856,329 or 801,531, the characteristics of polymer substrates may be modified and/or improved by grafting a coating on the surface of said substrates. The grafted polymer layer may be obtained by means of a radical graft polymerisation reaction starting from ethylenic unsaturated monomers. The radical graft polymerization reaction may be induced by ionizing radiation. A typical ethylenic unsaturated monomer is methyl acrylate. An extended list of other suited monomers includes vinylidene chloride. By means of the grafted coating, a number of different characteristics may be obtained or improved; however, the preparation of a coating comprising biocompatible characteristics is not stated. When grafting within a liquid phase, there is a danger of covering and closing the fine and ultra-fine pores of a porous hollow fiber.

Contrary thereto, there is a still existing demand for a relatively simple method of preparing in high productivity a biocompatible porous hollow fiber comprising a biocompatible carbon material which is chemically bound to the surface of a porous hollow fiber without substantially decreasing or eliminating the porosity of said hollow fiber.

SUMMARY OF INVENTION

Accordingly, it is an object of the present invention to provide a biocompatible porous hollow fiber made of a polyolefin material and having a coating of biocompatible carbon material, wherein the carbon material is chemically bound to the hollow fiber and wherein a sufficient porosity of the porous hollow fiber is retained.

It is a further object of the present invention to provide a method of manufacture the biocompatible porous hollow fiber using relatively simple process steps and providing high productivity and a constant quality of the product. Especially, the method shall provide a coating of a carbon material having excellent compatibility with respect to blood (haemocompatibility) and high thromboresistance.

It is another object of the present invention to propose specific kinds of use of the biocompatible porous hollow fibers.

In general, the biocompatible porous hollow fiber according to the present invention comprises a porous hollow fiber structure made of a polyolefin material and having a coating of a biocompatible carbon material, wherein the biocompatible carbon material has been obtained by the following sequence of steps:

introducing a preformed porous hollow fiber into an atmosphere of gaseous monomer vinylidene chloride (1,1 di-chloro ethylene);

inducing a graft-polymerization reaction and grafting a uniform layer of polyvinylidene chloride on the porous hollow fiber; and substantially eliminating and removing hydrogen chloride (dehydrochlorination reaction) from the polyvinylidene chloride layer in order to convert the polyvinylidene chloride layer into a coating of biocompatible carbon material.

Preferably, the dehydrochlorination reaction has been performed to such an extent that a residual chlorine content of said layer or coating amounts less than 6% based on the chlorine content of the original polyvinylidene chloride layer.

Typically, a thus obtained coating may comprise a thickness larger than 5 microns, is chemically bound to the substrate material and consists essentially of a pure carbon material comprising excellent biocompatible characteristics. The gas phase graft-polymerization reaction and the dehydrochlorination reaction may be effected under those conditions which do not affect substantially the mechanical properties of the fiber material. In addition, the original porosity of the porous hollow fiber structure is retained in a large and sufficient extent. The coating is flexible and is bound inseparably to the fiber material. Practically the coating may comprise a coating thickness varying in a large range according to the specific demand. Sometimes a very high coating thickness may decrease the porosity.

A further important aspect of the present invention is related to a method of manufacturing said biocompatible porous hollow fiber. The method according to the present invention comprises the following steps:

providing a prepared porous hollow fiber made of a polyolefin material;

introducing the hollow fiber into a reactor vessel equipped for hermetic sealing;

providing an atmosphere of gaseous monomer vinylidene chloride (1,1 di-chloro ethylene) within the reactor vessel;

inducing within the reactor vessel a graft polymerization reaction and grafting a uniform polyvinylidene chloride layer on the porous hollow fiber;

exposing the porous hollow fiber substantially covered with a polyvinylidene chloride layer to conditions which cause a substantial elimination and removal of hydrogen chloride (dehydrochlorination reaction) from the polyvinylidene chloride layer in order to convert the polyvinylidene chloride layer into a coating comprising a biocompatible carbon material being chemically bound to the polyolefin material of the porous hollow fiber.

According to a preferred embodiment of the present invention, said dehydrochlorination reaction will be at least continued until a residual chlorine content of the coating amounts less than 6% based on the chlorine content of the original polyvinylidene chloride layer.

A further important aspect of the present invention is related to specific kinds of use of said biocompatible porous hollow fiber as exchange material, diaphragm and/or semipermeable membrane or as an intermediate product to provide those exchange materials, diaphragms and/or semipermeable membranes within devices which will contact blood or plasma outside of the living body. For example, those devices may include oxygenators, dialyzers, haemo concentrators, blood filter, blood defoaming apparatuses, dialyzer filter devices and other filter devices and other components of an extra-corporal blood circulation system, such as a heart-lungs-machine.

BEST AND VARIOUS MODES FOR CARRYING OUT INVENTION

Figure 1:
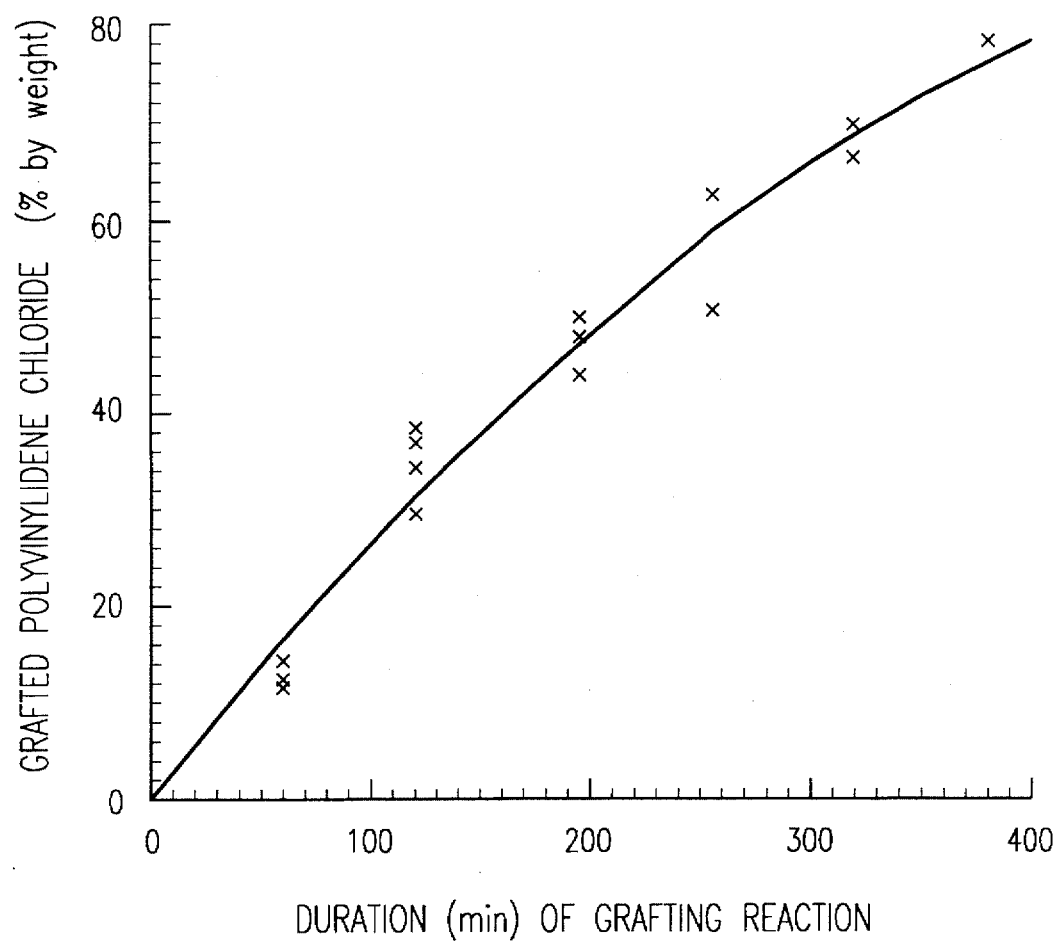
FIG. 1 is a graph of the amount of grafted polyvinylidene chloride versus time.

In the following, the invention will be explained in more detail.

Conventional and commercially available porous hollow fibers may be used as starting material for the biocompatible porous hollow fibers according to the present invention. The fiber material as used within the scope of the present invention is a fiber-forming polyolefin material. Suitable polyolefin materials include especially polyethylene and polypropylene and other higher $\alpha$-olefins. Especially preferred are porous hollow fibers made of a polypropylene material. The term "polypropylene material" shall include all kinds of polypropylene polymers which are used in the medical and biological field, including polypropylene copolymers with other $\alpha$-olefins, polypropylene homopolymers and mixtures of different polypropylene polymers. Further, modified polypropylene materials may be used comprising a molecular weight which has been reduced and selected in specific ranges in order to provide distinctive mechanical properties. As known in the art, a specific reduction of the molecular weight of polypropylene materials may be obtained by radical reaction with peroxid or similar reagents.

Other polymers which are commonly used in the medical field are less suited as fiber materials with the present invention. For example, polytetrafluoroethylene (TEFLON) would be destroyed by the $\gamma$-radiation which is preferably used for inducing the radical graft polymerization reaction. Polyesters, such as DACRON, would be hydrolyzed by the conditions provided for the dehydrochlorination reaction of the polyvinylidene chloride.

The starting material is a porous hollow fiber comprising a porosity which provides a gas exchange or an exchange of dissolved substances (dialysis) between two liquid phases separated from each other by the porous wall structure of the hollow fiber, wherein a passage of liquid through the pores of the hollow fiber is hindered. Typically, the pores comprise dimensions less than 1 micron. The coated porous hollow fibers shall comprise a porosity of from 10 to 50%, preferably a porosity of from 20 to 40%. The deposition of polyvinylidene chloride by a graft polymerisation reaction may cause a decrease of the original porosity, especially when grafting more than 40 to 50% by weight polyvinylidene chloride, based on the weight of the original porous hollow fiber. Preferably, the starting porous hollow fiber comprises an especially high porosity in order to compensate a slight decrease of porosity caused by the deposition of polyvinylidene chloride. It is still a surprising aspect that this kind of process allows to obtain a kind of porous composite material comprising a coating of biocompatible carbon material which improves substantially the haemo compatibility and thromboresistance of a porous hollow fiber without substantially eliminating the original porosity of the porous hollow fiber structure. The present new material comprises a true composite material because the biocompatible carbon material is inseparably bound to the fiber material by covalent C—C bonds.

Preferably, oriented porous hollow fibers will be used. The orientation of the carbon chain obtained by drawing the starting porous hollow fibers facilitates the deposition of a uniform coating of biocompatible carbon material. Preferably, the gas phase graft polymerization reaction may be effected under those reaction conditions which provide an epitaxial growing of the polyvinylidene chloride layer on the larger part of the fiber material surface. The grafted polyvinylidene chloride does not form "hairs" or similar structures, but does form a layer which covers essentially completely the underlaying surface of the fiber material. The grafted polyvinylidene chloride layer similates or adopts the structure of the underneath fiber material. A previous drawing operation generates an orientation of the fiber material which provides a good starting structure for the following graft polymerization reaction.

The starting material for preparing the coating comprises monomer vinylidene chloride (1,1 di-chloro ethylene). Commercially available pure and stabilized preparations comprise a purity of more than 99.5%. Monomer liquid vinylidene chloride comprises a boiling point of about 30° to 32° C. Preferably, a de-gasing treatment of the monomer liquid vinylidene chloride at reduced pressure will be effected prior to the use thereof. The monomer vinylidene chloride starting material shall be free of air.

Preferably, the liquid monomer vinylidene chloride may be poured or sucked into an evaporator vessel which is arranged distantly to the reactor vessel and connected with said reactor vessel via a pipe or tube. The liquid monomer vinylidene chloride is evaporated within said evaporator vessel in order to generate gaseous monomer vinylidene chloride which is fed into the reactor vessel through said pipe or tube. The pipe or tube is equipped with valve means in order to control the amount and the vapor pressure of the gaseous vinylidene chloride fed into the reactor vessel. The evaporation rate may be controlled in order to maintain the vapor pressure of the vinylidene chloride within the reactor vessel within a certain range. Preferably, the vapor pressure of monomer vinylidene chloride within the reactor vessel is maintained below 1 bar.

The method according to the present invention provides for inducing a graft polymerization reaction within a gas phase of monomer vinylidene chloride in order to graft or deposit a uniform layer of polyvinylidene chloride on the porous hollow fiber structure. The graft polymerization is based on a radical polymerization reaction. The present graft polymerization may be induced on several ways, for example by means of a laser light activation. Basically, the graft polymerization procedures as disclosed in the above-referred British Patents 856,329 and 801,531 may be used; however, the uniformity and regularity of the grafted polyvinylidene chloride layer and the yield to be obtained would be poor. According to a preferred aspect, the present invention looks for a radiation induced graft polymerization reaction by means of ionizing radiation which provides a chemical bonding of the coating via covalent C—C bonds to the fiber material in order to obtain a true composite material. Preferably, the radiation source comprises especially a gamma radiation source. Gamma rays comprise a high penetration power. The radiation may penetrate through the material of the reactor vessel, for example stainless steel. Several hermetically sealed reactor vessels may be arranged adjacently to a single gamma radiation source in order to induce and perform the graft polymerization reaction within said vessels. A radiation by electron beams emanating from an electron accelerator device would be less suited because only relatively thin layers could be activated by an electron radiation. A well suited and preferred gamma radiation source according to the present invention comprises the $^{60}_{27}Co$ isotope.

When grafting polyvinylidene chloride on oriented porous polypropylene hollow fibers by means of the radiation induced graft polymerization reaction according to the present invention, those conditions would be preferred which yield within the reactor vessel a dose rate of from 0.1 to 1.5 watt per kg radiated material; this corresponds to 10 to 150 rad/sec. Preferably the radiation may be continuously operated throughout the complete duration of the graft polymerization reaction.

By means of this radiation induced gas phase graft polymerization reaction a uniform polyvinylidene chloride layer may be obtained and chemically bound to the polyolefin material of the porous hollow fiber without impairing the mechanical characteristics of the fiber material and without a complete elimination of the original porosity. The polyvinylidene chloride is bound via covalent C—C bonds to the carbon chain of the polyolefin fiber material. The layer thickness of the grafted polyvinylidene chloride layer may be varied in a wide range as long as the original porosity will be retained in a sufficient extent.

Preferably, such an amount of polyvinylidene chloride will be deposited, which will reduce the strength and the porosity of the original porous hollow fiber only in an accepted degree, and which will provide subsequently to the dehydrochlorination reaction a coverage or a coating of carbon material which will substantially improve the haemo compatibility and the thromboresistance of the treated porous hollow fiber compared with the original porous hollow fiber. Evidently, only a coverage or coating of those areas and "active spots" of the fiber surface is necessary and important which may be contacted by the blood and by the active blood components.

The fore-mentioned radiation induced graft polymerization reaction may be preferably effected within a still gas phase consisting of monomer vinylidene chloride. Furthermore, it is helpful to move the starting hollow fiber with respect to the radiation source. In the case of coils consisting of wound-up porous hollow fibers, such coils may be rotated continuously around their axis. Furthermore, it is preferred to use relatively mild reaction conditions and an extended reaction duration instead of strong conditions within a short term. During the graft polymerization reaction the forming of a liquid vinylidene chloride phase on the hollow fiber and/or within the reactor vessel is to be avoided. Grafting from a liquid vinylidene chloride phase would yield non-uniform products. Preferably, the pressure of the gas phase consisting of monomer vinylidene chloride is maintained in the range of from about 500 to 700 mbar (millibar). Under these conditions, the monomer vinylidene chloride will condense at a temperature of about 20° C. Preferably, the fiber material and the material of the wall of the reactor vessel will be maintained at a higher temperature. Especially preferred, the temperature of the fiber material and of the reactor vessel wall will be maintained in the range of from about 25° to 50° C. The graft polymerization reaction is an exotherm reaction, and during an extended duration of reaction the fiber temperature may raise to about 40° C. In case of a porous hollow fiber consisting of a polypropylene material, the preferred fiber temperature shall not exceed about 30° to 40° C. The dose rate of the radiation may be controlled accordingly in order to avoid a fiber temperature higher than 40° C. Preferably, the dose rate will be maintained within the range of from 0.1 to 1.5 watt per kg radiated material, as stated above. It is preferred to extend the duration of reaction instead of increasing the dose rate. Preferably, the radiation induced graft polymerization will be continuously performed for a duration of at least 20 hours; even a duration of 30 to 40 hours is not uncommon under practical conditions. Preferably, the radiation action will be continuously maintained during the complete duration of the gas phase graft polymerization reaction.

During this gas phase graft polymerization reaction the gaseous monomer vinylidene chloride penetrates the fiber material, for example a porous polypropylene hollow fiber and/or a coil made of wound-up polypropylene hollow fibers. Typically, the diffusion rate of the gaseous monomer vinyldene chloride is higher than the rate of consumption of gaseous monomer vinylidene chloride caused by the graft polymerization reaction. This diffusion rate may be influenced and increased with the temperature of the gaseous monomer vinylidene chloride. This means, the graft polymerization reaction proceeds from an equilibrate concentration of gaseous monomer vinylidene chloride. The formed polyvinylidene chloride will be chemically bound and anchored within the fiber material. Surprisingly, the originally present porosity of the starting porous hollow fiber will not be eliminated completely. Furthermore, the polyvinylidene chloride will grow uniformly on the accessible sections of the fiber surface and will form there a uniform and dense coating. It is preferred to maintain such reaction conditions which cause a structure of the polyvinylidene chloride layer which resembles the structure of the fiber material (epitaxial growing or deposition process). This kind of homology of structures is helpful to obtain an orientated layer of a distinctive carbon material providing biocompatibility. The growing or depositing of the polyvinylidene chloride layer is not limited by inherent factors and might be continued as desired as long as a sufficient porosity and strength of the porous hollow fiber is retained.

In general, all these reaction conditions will be optimized in order to obtain under mild conditions a uniform polyvinylidene chloride layer which is chemically bound to the fiber material without undue impairing the starting porous hollow fiber and the porosity thereof. Even coils of polypropylene hollow fibers may be treated under these conditions.

On porous hollow fibers made of polypropylene preferably 0.1 to 1.2 parts per weight of polyvinylidene chloride may be deposited on 1 part per weight of fiber material under these conditions of a radiation induced gas phase graft polymerization reaction. Even more preferred, 0.4 to 0.6 parts per weight of polyvinylidene chloride may be deposited on 1 part per weight of fiber material.

Using the fore-mentioned conditions, preferably 40 to 60 parts per weight of polyvinylidene chloride may be grafted on a fiber coil consisting of 100 parts per weight of porous polypropylene hollow fibers, such that the coated fiber coil will comprise a complete weight of 140 to 160 parts per weight following the graft polymerization reaction. Only such an amount of polyvinylidene chloride is required, which will form subsequently to the dehydrochlorination reaction a coverage or coating of biocompatible carbon material which will substantially improve the haemo compatibility, here especially with respect to haemolysis, depositing of leukocytes, activation of the complement complex and activating the blood coagulation cascade until to the thrombus forming of these treated porous hollow fibers in comparison with non-treated original hollow fibers of the same kind. On the other hand, the deposition of polyvinylidene chloride shall be kept as low as possible, as far as the desired haemo compatibility will be obtained, in order to impair the original porosity of the starting fiber and the mechanical properties thereof not more than necessary.

In consideration of these side conditions, it is preferred to graft about 40 to 60 parts per weight polyvinylidene chloride on 100 parts per weight hollow fiber material, especially polypropylene. Following a substantially complete removal of hydrogen chloride during the dehydrochlorination treatment, about 10 to 15 parts per weight carbon material will remain on 100 parts per weight hollow fiber material. Or stated in other words, a coated porous hollow fiber obtained under these conditions will comprise about 9 to 13% by weight carbon material based on the complete weight of the coated porous hollow fiber.

Hydrogen chloride (HCl) has to be eliminated and removed substantially complete from the thus obtained polyvinylidene chloride layer in order to convert said polyvinylidene chloride layer into a coating consisting essentially of a pure carbon material having biocompatible characteristics. This reaction is termed dehydrochlorination reaction. Further, those conditions of the dehydrochlorination reaction have to be selected which cause a minimum of damage or impairment of the fiber material, and here especially of the mechanical properties of the fiber material.

In the case of foils and entire fibers made of polypropylene, efforts have been made to perform said dehydrochlorination reaction by means of metallic sodium and/or sodium amide within liquified ammonia. Basically, this type of reaction is possible in a laboratory scale, but requires a very extended duration of reaction of 100 hours and more and further requires working under a high pressure (50 bar and more) within an autoclav. The productivity of this type of reaction is too poor for working in an industrial scale. Further, non-reacted sodium amide has to be decomposed and removed, for example by means of a substantial amount of methanol.

Further efforts have been made to perform the dehydrochlorination reaction by means of gaseous ammonia in a gas phase reaction. Basically, this kind of reaction is possible, but in a practical operation only very small samples have been successfully treated. A sufficient rate of reaction requires temperatures above 100° C. On the other hand, the fiber temperature, shall not exceed temperatures of 100° to 120° C. The dehydrochlorination reaction is an exotherm reaction. When working in a gas phase environment, there is only a limited possibility of heat elimination, and therefore, an overheating of the fibers may occur easily. Further, when working in an ammonia gas phase, the ammonium chloride ($NH_4Cl$) formed by the dehydrochlorination reaction within an ammonia atmosphere cannot be removed easily.

It is an essential object of the present invention to provide conditions of a dehydrochlorination reaction which are suited for working in an industrial scale, which do not substantially impair the mechanical properties of the hollow fiber structure and material, and which eliminate and remove hydrogen chloride (HCl) to a substantial amount from said polyvinylidene chloride in order to convert the polyvinylidene chloride layer to a coating of a biocompatible carbon material. Preferably, the dehydrochlorination reaction shall reduce the residual chlorine content of the carbon coating to less than 6%, based on the chlorine content of the original polyvinylidene chloride layer. Even more preferred is a residual chlorine content in the carbon coating of less than 3%, based on the chlorine content of the original polyvinylidene chloride layer.

According to a preferred and essential aspect of the present invention, this dehydrochlorination reaction will be performed by means of a hot aqueous alkaline solution. Preferably, the porous hollow fiber comprising the grafted polyvinylidene chloride layer will be dipped into a hot aqueous alkaline solution and will be maintained within said solution for at least several hours. Alternatively, the hot aqueous alkaline solution may be pumped through a reactor chamber wherein the porous hollow fiber comprising the grafted polyvinylidene chloride layer being arranged within said reactor chamber. In case of coils consisting of porous polypropylene hollow fibers and being coated with a grafted polyvinylidene chloride layer, the hot aqueous alkaline solution may be pumped through the coils which are arranged within a reactor vessel.

Preferred is a treatment at or below the boiling temperature of the aqueous solution. A temperature of the aqueous solution of about 80° to 100° C. has proved quite effective and may be preferred.

When working at a temperature at or below 100° C., an impairment of the porous hollow fiber material and structure may be avoided. The boiling point of the solution avoids a higher fiber temperature. Further, an aqueous solution comprises a high thermal capacity. When working within an aqueous solution, a higher rate of reaction may be obtained and controlled, because the heat developed by the exothermic dehydrochlorination reaction may be eliminated easily. The chloride salt formed by the dehydrochlorination reaction dissolves easily within an aqueous solution and may be removed easily.

In order to provide an aqueous alkaline solution the typical alkaline reagencies such as inorganic bases and salts may be used, for example sodium hydroxide or potassium hydroxide or the carbonates and bicarbonates of alkali metals and alkaline earth metals. Organic bases such as amines did not provide satisfying results. When working in an aqueous NaOH or KOH solution, it might be helpful to add a phase transfer catalyst such as for example tetrabutylammoniumbromide (($CH_3CH_2CH_2CH_2)_4NBr$).

A most preferred dehydrochlorination agent is hot concentrated aqueous ammonia. An ammonia concentration of 20 to 35% by weight has proved good results. Preferably, the commercially available concentrated aqueous ammonia (ammonia hydroxide) may be used comprising an ammonia concentration of about 25% by weight. According to a further preferred aspect an aqueous ammonia solution will be used which is ammonia saturated at the given temperature, and a necessary excess pressure of gaseous ammonia will be provided. For example, an excess pressure of ammonia of from about 6 to 8 bar may be provided. For example, especially good results have been obtained under the following conditions:

a hot aqueous ammonia comprising an ammonia concentration of about 25% by weight;

an operation temperature of about 96° C. and an excess pressure of ammonia of about 6 bar.

Under these relatively mild dehydrochlorination conditions, the dehydrochlorination reaction by means of hot concentrated aqueous ammonia will be maintained for a duration which is sufficient for a substantial elimination and removal of hydrogen chloride from the polyvinylidene chloride and to convert the polyvinylidene chloride into a coating of a biocompatible carbon material. Typically, a duration of at least 20 hours may be required. According to a preferred embodiment of the present invention, this type of dehydrochlorination reaction by means of hot concentrated aqueous ammonia shall reduce the residual chlorine content of the carbon coating to less than 6 % based on the chlorine content of the original polyvinylidene chloride layer. In this case, the dehydrochlorination reaction may be performed for a duration of about 30 to 40 hours and more.

Even more preferred, the dehydrochlorination reaction may be performed for a sufficient duration in order to reduce the residual chlorine content of the coating to less than 3% based on the chlorine content of the original polyvinylidene chloride layer. The chlorine forming the residual chlorine content of the coating is termed "the structurally bound chlorine", i.e. the chlorine contained in residual amounts of polyvinylidene chloride within the carbon coating. This structurally bound chlorine may be detected by means of infrared spectroscopy at absorption bands at about 1050 $cm^{-1}$. A residual content of structurally bound chlorine of less than 3% will provide a coating consisting essentially of a pure carbon material comprising outstanding biocompatible characteristics.

Following the dehydrochlorination reaction, a carbon material will be obtained having a density of about 1.8 $g/cm^3$. Spectroscopic measurements by means of infrared spectroscopy confirm absorption bands at 2180 $cm^{-1}$ and wide absorption bands at about 1600 $cm^{-1}$. The absorption bands at 2180 $cm^{-1}$ will be adopted to the stretching vibrations of C≡C triple-bonds in linearly conjugated carbine structures. The absorption bands at 1600 $cm^{-1}$ will be adopted to conjugated C=C double-bonds. According to this experimental results the inventors assume—without any acceptance to be bound to this proposal—that the substantially exhaustive dehydrochlorination reaction of the grafted polyvinylidene chloride layer will provide a carbon material having an oriented carbine structure.

Hydrophobic surfaces are characterized by high water contact angles, whereas hydrophilic surfaces exhibit small water contact angles. A conventional polypropylene foil as used for packaging purposes and having a thickness of about 50 to 60 μm comprises (as measured by means of the sessile drop method with a gonimeter at room temperature) a water contact angle of 92.5°, a blood contact angle of 88° and a blood plasma contact angle of 88.4°. Following a coating of the same polypropylene foil with a biocompatible carbon coating according to the present invention the same but coated polypropylene foil comprises a water contact angle of 47°, a blood contact angle of 55° and a blood plasma contact angle of 54°. This extraordinarily high decrease of the water contact angle confirms that the carbon coated surface according to the present invention is much more hydrophilic than the original polypropylene surface.

Typically, the content of the thus formed carbon material may range of from about 5 to 20% by weight based on the complete weight of a coated polypropylene hollow fiber or yarn; this means, the final coated porous hollow fiber comprising a coating of biocompatible carbon material is consisting of 80 to 95% by weight of polypropylene material and is consisting of 20 to 5% by weight of the carbon material, each based on the complete weight of the coated hollow fiber.

Following the dehydrochlorination reaction, the coated hollow fiber will be subjected to an extended washing or rinsing treatment, preferably by means of hot water in order to especially remove ammonium chloride. The content of ammonium chloride may be detected by means of infrared spectroscopy at absorption bands at about 1400 $cm^{-1}$. Preferably, the residual content of ammonium chloride shall be reduced to less than 0.1% by weight based on the complete weight of the coated fiber material. In order to achieve this goal, a several hours washing treatment using hot water with a temperature of about 80° to 90° C. is well suited.

Following the washing or rinsing treatment, a heat treatment may be provided which causes a relieve of strains within the elongated fiber structure. Preferably, the heat treatment may be performed within a vacuum drier cabinet comprising a reduced pressure less than 0.1 mbar, whereby a pumping operation will be maintained continuously. In case of coils made of wound-up coated hollow fibers, a sufficient heat treatment may be achieved at a temperature of 135° C. for a duration of about 1.5 hours within vacuum space. In addition, the type of heat treatment will remove residual traces of ammonium chloride by sublimation. Further, for the manufacture in an industrial scale and according to a preferred embodiment of the present invention the starting porous hollow fibers may be wound under controlled conditions on a perforated coil carrier such as a sleeve, a bobbin or a cartridge in order to obtain coils. The coils are introduced into the reactor vessel and the gas phase graft polymerization reaction will be effected with those coils. Thereafter, the treated coils will be introduced in another reactor vessel for effecting the dehydrochlorination reaction, and the dehydrochlorination reaction will be effected by means of a hot concentrated aqueous ammonia solution. The reaction proceeds through the coil and effects the complete wound-up material. Herewith, it is recommendable to maintain the thickness of the wound-up fiber material on the perforated coil carrier less than about 20 mm and/or to maintain the density of the wound-up fiber material in a range of from about 0.40 to about 0.60 $g/cm^3$. Maintaining these conditions will provide a good penetration of the complete fiber material by gaseous monomer vinylidene chloride or by aqueous ammonia. Several coils of said type may be introduced concurrently into a reactor vessel for the radiation induced gas phase graft polymerization reaction and may be treated concurrently. When performing the dehydrochlorination reaction, preferably each single coil will be introduced in an own apartment or chamber within the reactor vessel in order to obtain a good penetration of the wound-up fiber mass by means of a forced flow of hot aqueous ammonia. However, several reactor vessels may be arranged parallel and combined to a group of vessels; the hot alkaline dehydrochlorination agent, especially hot concentrated aqueous ammonia, may be pumped serially through each vessel of said group of vessels. Despite the relatively extended duration of treatment, a high productivity may be obtained when using such a group of vessels for performing the dehydrochlorination reaction.

There are hints that grafting polyvinylidene chloride on specific types of a continuous porous hollow fiber may increase the original length of the hollow fiber. For the time being, the reason for the elongation are not completely understood. Obviously, said length gain depends on the specific type of porous hollow fiber, or on the degree of porosity and/or on the structure of the micro pores of the porous hollow fiber. A similar length gain will not be observed when grafting polyvinylidene chloride on an entire fiber or yarn of polypropylene. When grafting 60 parts per weight polyvinylidene chloride on 100 parts per weight porous polypropylene hollow fiber, the porosity thereof has been obtained by a subsequent drawing step, a length gain of about 8% is observed, based on a given length section of the starting porous hollow fiber. Due to this fiber elongation, a given coil of wound-up continuous porous hollow fiber becomes more loose during the graft-polymerization reaction. In order to avoid this loosening of the continuous porous hollow fiber wound-up on a coil carrier, it is preferred to use a split coil carrier comprising a spring means which will push the several coil carrier parts in opposite directions. Such a split coil carrier may increase its effective circumference under the resiliency of the spring means, thus compensating for the elongation of the continuous porous hollow fiber to be treated and providing a strong and regular wound-up fiber coil during the complete graft-polymerization reaction.

Further, it is recommendable to recoil the coated continuous porous hollow fiber on a new coil carrier subsequently to the gas phase graft polymerization reaction and prior to the dehydrochlorination reaction in order to start the dehydrochlorination reaction with a new coil comprising the appropriate fiber coil density, which is well suited for the following dehydrochlorination reaction in a liquid phase. The hot aqueous solution may be pumped continuously through the perforated coil carrier and the coiled fiber mass wound-up on said coil carrier.

The following examples serve for a further explanation of the invention and may by no means be construed for a limitation of the invention.

Non-inventive Example (entire fiber)

This non-inventive example concerns the deposition of a coating made of a biocompatible carbon material on the circumference of an entire fiber of polypropylene material and serves for a general explanation of the present new technology.

The starting material is a multi-filament yarn comprising 36 orientated filaments each made of polypropylene. The multi-filament yarn comprises a length-related mass of 8 tex. For performing the steps of the method according to the present invention, said starting yarn will be re-coiled on a cylindric perforated cartridge consisting of a non-corrosive steel material and comprising a length of 185 mm and an external diameter of 30 mm. The re-coiling will be performed under conditions such as to obtain a wound-up yarn coil comprising a coil thickness of about 14 mm and comprising a coil density of about 0.50 to 0.55 g/cm$^3$. Accordingly, each coil will comprise about 170 to 180 g wound-up yarn.

The radiation induced gas phase graft polymerization reaction will be effected by introducing said coils into a gaseous phase of monomer vinylidene chloride and by additionally providing a radiation action. Accordingly, the coils will be introduced into a hermetically sealable reactor vessel equipped for evacuation. Preferably, the coils may be arranged within the reactor vessel for a rotation about the coil axis. A container comprising an evaporator is arranged distantly to the reactor vessel and is connected with the reactor vessel via a pipe or tube being equipped with a shut-off valve. The container is additionally connected to a vacuum pump for evaporation and for a de-gasing treatment. The liquid monomer vinylidene chloride will be poured into the container and will be evaporated by means of the evaporator arranged within said container.

Having inserted several coils into the reactor vessel, the reactor will be closed and will be evacuated to a residual pressure of about 10 mbar. The liquid, monomer vinylidene chloride, which has been previously de-gased under vacuum, will be introduced into the container. The introduced amount of vinylidene chloride is related to the complete amount of yarn to be coated and to the desired coating thickness. Following the introduction of vinylidene chloride into the container, the vinylidene chloride within the container will be de-gased again. As far as necessary, the evaporator will be set into operation in order to generate gaseous monomer vinylidene chloride within the container. Thereafter, the check valve will be opened in order to form a gas phase of monomer vinylidene chloride within the reactor vessel at ambient temperature. The temperature of the reactor vessel will be maintained at about 20 to 30° C.

The vapor pressure of monomer vinylidene chloride will be controlled between about 500 and 700 mbar (millibar). Care shall be taken in order to avoid any condensation of liquid vinylidene chloride on the fiber coil and/or on the walls of the reactor.

The radiation action will be performed by means of one or more radiation source(s) comprising the radioactive

$$^{60}_{27}\text{Co}$$

isotope. Thereto, the reactor vessel will be arranged within a safe-guarded room equipped such that the radiation source(s) may be introduced into the room from a shielded position. For example, regularly the radiation source(s) may be positioned within a deep hole in the ground beneath the floor of the room. In order to provide the radiation action, the radiation source(s) will be raised from said hole into the room and will be arranged adjacent to the reactor vessel such that the gamma radiation flux may penetrate the reactor vessel. The radiation source(s) and other conditions will be controlled such as to obtain within the reactor vessel a radiation dose rate of about 0.15 watt per kg radiated material; this corresponds to a radiation dose rate of about 15 rad/sec. The container containing the liquid vinylidene chloride is arranged distantly to the radiation source(s) and to the reactor vessel, and may be shielded with respect to the gamma radiation by means of lead bricks. The exposure of the reactor vessel to the radiation action will be continuously maintained during the complete graft polymerization reaction. The coils within the reactor vessel may be rotated, and the speed of rotation may be adjusted to and controlled along with the radiation dose rate.

When starting the radiation induced graft polymerization reaction the liquid polyvinylidene chloride within the container may have temperature of about 17° to 20° C. The radiation induced graft polymerization reaction is an exothermic reaction, and the heat developed during the reaction will increase the temperature of the yarn coil to about 35° to 40° C. The yarn temperature shall not exceed a temperature of about 40° C. A duration of reaction of about 30 to 35 hours is required, in order to deposit about 65 to 80 parts per weight polyvinylidene chloride on 100 parts per weight polypropylene yarn under these conditions. The reaction is terminated by a decrease of pressure within the system, which is caused by a consumption of the monomer vinylidene chloride. Following the termination of the reaction, the radiation source(s) will be moved toward its/their originally shielded and protected position. The volatile matters including residual vapors of vinylidene chloride within the reactor vessel will be pumped out and condensated within a cooling trap cooled by means of liquid nitrogen. Thereafter, fresh air is blown through the reactor vessel. The coils comprising the coated yarn will be removed out of the reactor vessel. The coated yarn has a white lustrous appearance.

Following the radiation induced graft polymerization reaction, the coated yarn is re-coiled onto another perforated coil carrier in order to obtain again coils comprising a density which is suited for the following dehydrochlorination reaction.

The dehydrochlorination reaction will be effected by pumping hot aqueous ammonia solution comprising 25% per weight ammonia through the perforated coil carrier and through the fiber coil wound-up on the carrier. The process is controlled by means of the differences in temperature and/or pressure within a feeding container and a receiving container for the aqueous ammonia solution. Each coil will be placed within a single apartment or chamber of a reactor vessel or within a single reactor vessel.

The complete installation comprises a number of apartments, chambers or reactor vessels being connected in a serial arrangement. Before starting the dehydrochlorination reaction the complete installation will be evacuated to a residual pressure of about 0.1 mbar. In the following the aqueous ammonia will be pumped into the feeding container and will be heated to the prescribed temperature. This hot aqueous ammonia will be pumped out of the feeding vessel through the perforated coil carrier and through the fiber coil wound-up on said carrier into a receiving container and in the following out of the receiving container through the coil carrier and the fiber coil into the feeding container. Essentially the aqueous ammonia comprises a temperature of 96° C., an ammonia concentration of 25% per weight, and within the closed installation there is an ammonia pressure of about 6 bar above the liquid aqueous ammonia solution. Maintaining these conditions the dehydrochlorination reaction will be performed for a duration of about 35 hours.

In the following, the treated fibers will be rinsed with hot water in order to remove ammonium chloride which has been formed as by-product. For performing said rinsing or washing treatment hot desalted water comprising a temperature of 80° to 95° C. will be pumped through the fiber coil for a duration of 5 hours.

In the following, a heat treatment of the dehydrochlorinated and rinsed yarns will be performed in order to relieve strains within the elongated fiber structure and in order to avoid a thermal shrinkage during a subsequent use of the yarns (for example at a sterilization treatment using elevated temperatures) and in order to completely remove residual traces of ammonium chloride by sublimation. For said heat treatment the fiber coils will be maintained for at least 1.5 hours within a vacuum drier cabinet under a vacuum less than 0.1 mbar at a temperature of about 135° C.

Following the heat treatment, yarn samples may be analysed in order to verify the residual amount of structural chlorine and of ammonium chloride. The "structurally bound chlorine" means chemically bound chlorine being contained within residual amounts of polyvinylidene chloride. This chemically bound chlorine may be detected by means of infrared spectroscopy at absorption bands at about 1050 cm$^{-1}$. Maintaining the above-mentioned conditions of a dehydrochlorination treatment, yarn coils may be obtained which contain less than 3% structurally bound chlorine based on the residual chlorine content of the original polyvinylidene chloride layer. Further, these yarn coils comprise less than 0.1% ammonium chloride based on the weight of the coated fiber or yarn. The coated yarn has a dull, deep black appearance and is consisting of 87% per weight of polypropylene and of 13% per weight of a biocompatible carbon coating, based on the weight of the coated yarn.

EXAMPLE

This example concerns the preparation of biocompatible porous hollow fibers according to the present invention.

The starting material is a conventional continuous porous hollow fiber made of polypropylene, as sold by HOECHST CELANESE CORPORATION under the trade designation "CELGARD X 10 240" comprising a porosity of 30% or under the trade designation "CELGARD X 20 240" comprising a porosity of 40%. According to the manufacturer's specification, these hollow fibers have an outside diameter of 300 μm, an inside diameter of 240 μm and a wall thickness of 30 μm. The porosity is 30% or 40% as measured according to the U.S. STANDARD ASTM D-2873. The pores have dimensions, that is a length dimension x a width dimension of about 0.15 μm×0.05 μm. These conventional continuous hollow fibers have been wound-up in amounts of about 1 to 10 g on perforated cartridges made of titanium. These wound-up hollow fiber coils are arranged within a reactor vessel equipped for a hermetically sealing and suited for radiation chemical experiments. An evaporator vessel is connected via a tube with the reactor vessel. Monomer liquid vinylidene chloride is poured into the evaporator vessel. The liquid monomer will be degassed by a vacuum treatment. The reactor vessel may be brought and arranged within a radiation field provided by a gamma radiation source being equipped with the isotope $$^{27}_{60}Co.$$

Those conditions have been selected which will provide within the reactor vessel an average dose rate of about 1.4 W/kg radiated material (this dose rate corresponds to about 140 rad/sec.) The radiation action will be continued during the complete gas phase graft-polymerization reaction. The reactor vessel will be maintained at the temperature of 30° C. The liquid monomer contained within the evaporator vessel comprises a temperature of 28°C.

Figure 2:
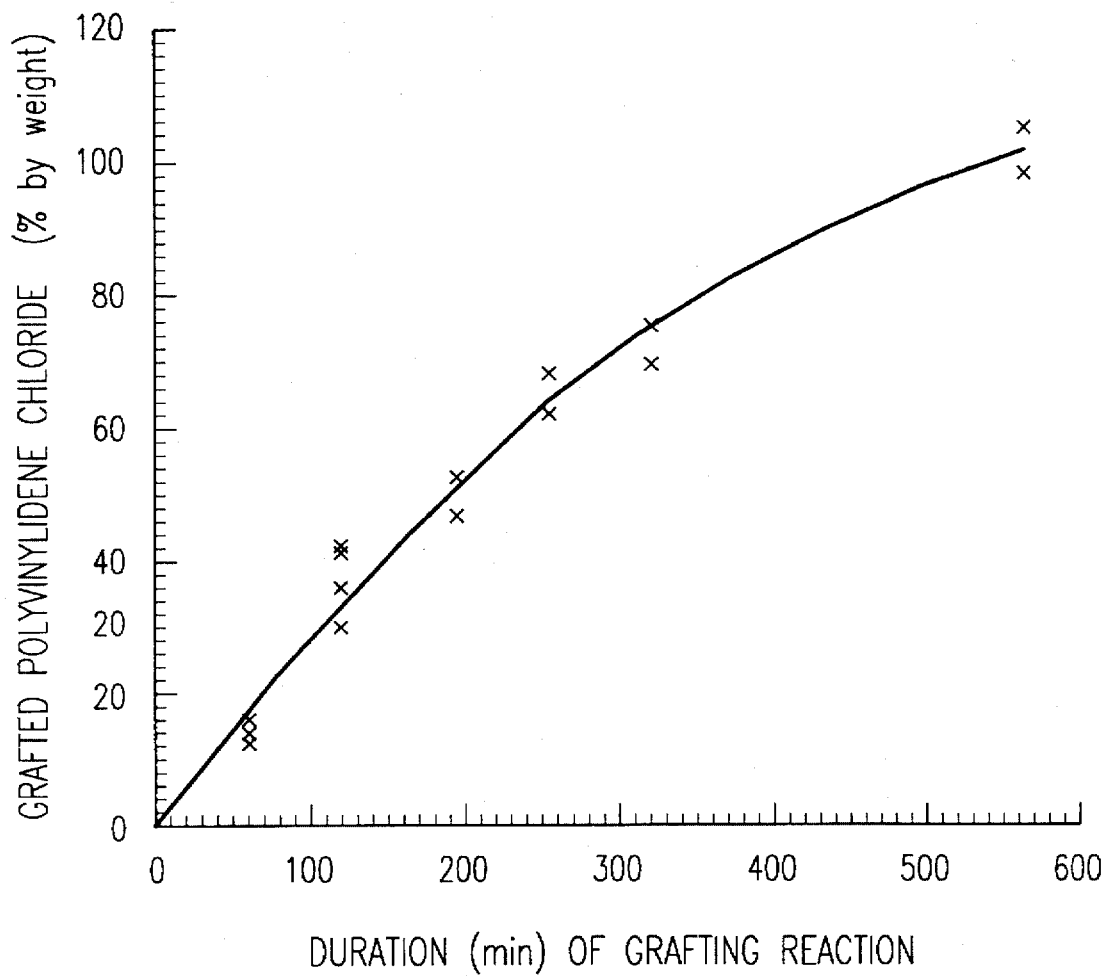
FIG. 2 is a graph of the amount of grafted polyvinylidene chloride versus time.

Subsequently to definite periods, the reactor vessel will be opened, and samples of the coated hollow fiber will be taken. The coated hollow fiber samples will be weighed out in order to determine the amount of deposited polyvinylidene chloride. FIG. 1 of the drawings shows the amount of graft-polymerized polyvinylidene chloride on a porous hollow fiber having a porosity of 30% in dependence of the duration of the graft-polymerization reaction. FIG. 2 of the drawings shows a similar presentation. concerning a porous hollow fiber comprising a porosity of 40%. The amount of deposited polyvinylidene chloride is stated in percent by weight based to the weight of the starting fiber. Evidently, there is an essentially linear dependency from the duration of graft-polymerization reaction until at least about 50% by weight polyvinylidene chloride has been deposited. The complete curve may be described as a polynomial of second order.

Contrary to the results obtained with a similar graft-polymerization reaction of entire polypropylene fibers, the graft-polymerization reaction on porous hollow fibers provides the surprising result of an increasing fiber length. Due to this elongation of the original fiber length, the density of the wound-up fiber coil becomes more loose, and there is a danger of twisting free windings. The increase of the fiber length during the graft-polymerization reaction has been measured. The results are shown with FIG. 3 of the drawings. The interrupted line concerns the porous hollow fiber having a porosity of 30%. The continuous line concerns the porous hollow fiber comprising a porosity of 40%. Evidently, grafting an amount of about 60% per weight polyvinylidene chloride on a continuous porous hollow fiber provides an increase of the original fiber length of about 8%. Despite the inventors do not completely understand this phenomenon, the inventors assume that the gaseous monomer vinylidene chloride may also enter fractures, fissures and pores being present in the fiber wall and providing the porosity. During the graft-polymerization reaction this vinylidene chloride being present within those fractures, fissures and pores may lead to an expansion of fiber layers in a length direction of the porous hollow fiber.

The thus obtained samples of coated porous hollow fibers having a coating of grafted polyvinylidene chloride are exposed to dehydrochlorination reaction conditions which cause delimination and substantial removal of hydrogene chloride (HCl), and additionally convert the polyvinylidene chloride layer into a coating of biocompatible carbon material. In detail, the coated samples are maintained for 30 hours within a hot concentrated aqueous ammonia solution comprising an ammonia concentration of 25% per weight. Following this dehydrochlorination reaction, the content of remaining "structural" chlorine is less than 6% per weight based on the chlorine content of the polyvinylidene chloride layer.

The dimensions of the starting fibers, of the coated porous hollow fibers following the graft-polymerization reaction and of the biocompatible porous hollow fibers obtained subsequently to the dehydrochlorination reaction have been measured. The results are listed in the following table.

TABLE 1

| Fiber | External diameter (μm) | Wall thickness (μm) | Inside diameter (μm) |
|---|---|---|---|
| Porous hollow fiber made of polypropylene and comprising a porosity of 30% | 311 | 26 | 259 |
| subsequently to grafting 30% by weight polyvinylidene chloride | 311 | 28 | 255 |
| subsequently to the dehydrochlorination reaction | 314 | 27 | 260 |
| subsequently to grafting 70% by weight polyvinylidene chloride | 316 | 28 | 260 |
| subsequently to the dehydrochlorination reaction | 303 | 28 | 247 |
| porous hollow fibers made of polypropylene and comprising a porosity of 40% | 313 | 26 | 261 |
| subsequently to grafting 30% by weight polyvinylidene chloride | 312 | 19 | 254 |
| subsequently to the dehydrochlorination reaction | 317 | 29 | 259 |
| subsequently to grafting of 53% by weight polyvinylidene chloride and subsequently to the dehydrochlorination reaction | 305 | 27 | 251 |

Obviously, the graft-polymerisation reaction and the dehydrochlorination reaction do not significantly change the dimensions of the starting porous hollow fiber.

A further experiment serves for an assessments of how much does the graft-polymerization and deposition of polyvinylidene chloride and the subsequent elimination and removal of hydrogene chloride (dehydrochlorination reaction) influence the original porosity of the porous hollow fibers. This assessment has been made indirectly by measuring the gas penetration capability of the fibers. For each measurement six fiber samples have been selected which comprise a fiber length of about 15 cm. These fiber samples are arranged within a glass tube and subjected to a little stretching The one ends of the hollow fibers are closed pressure-tight by means of a glueing agent. The other opposite fiber ends are connected pressure-tight to a container comprising pressurized air under an excess pressure of about 200 to 260 millibar above the atmospheric pressure. Maintaining similar conditions for each experiment, a decrease of the pressure within the container along with the running time has been measured. Under these conditions, a decrease of the gas pressure within the container may only be caused by a penetration of gas through the wall of the hollow fibers. The results obtained are shown with FIG. 4 of the drawings. Evidently, a such measured gas penetration capability decreases with an increasing amount of grafted polyvinylidene chloride deposited on the porous hollow fibers. Further, a decrease of that gas penetration capability is larger with a starting hollow fiber having a porosity of 30% than with a starting porous hollow fiber having a porosity of 40%. These results confirm, that even a starting porous hollow fiber having a porosity of 40% following a grafting and depositing of about 50% to 60per weight polyvinylidene chloride based on the weight of the starting fiber shows still about 60% of the gas penetration capability of the original starting fiber (=100% gas penetration capability). This demonstrates that the grafting and deposition of polyvinylidene chloride and the conversion of the polyvinylidene chloride layer into a coating of carbon material does not completely eliminate the original porosity. Actually a starting porous hollow fiber having an original porosity of 40% or even 50% may maintain a sufficient porosity after deposition of about 32% to 48% by weight polyvinylidene chloride which will form following the dehydrochlorination treatment about 8% to 12% by weight carbon material covalently bound to the polyolefin material of the porous hollow fiber. This coated porous hollow fiber will maintain a sufficient porosity for its intended use in oxygenators, dialyzers and similar devices, but comprises much better biocompatible properties than the original starting porous hollow fiber.

This means, by suited selection of the starting porous hollow fiber having a porosity as high as possible, and by suited selection of the graft-polymerisation conditions, coated porous hollow fibers may be obtained having still a sufficient porosity, but additionally comprising a covalently bound and therefore strongly adherent coating made of a biocompatible carbon material which increases the haemocompatible properties of the coated fibers significantly with respect to the non-treated starting porous hollow fibers.

Further experiments have been made in order to evaluate the change of mechanical properties, for example mechanical strength and breaking elongation caused by the graft-polymerisation reaction and by the dehydrochlorination reaction. Initial results of these experiments confirm, that it is not recommendable to graft much more than 60% by weight polyvinylidene chloride onto a porous hollow fiber.

Non-inventive Example (polypropylene foil)

A conventional polypropylene foil as used for packaging purposes and having a thickness of about 50 to 60 μm has been coated on both sides with a carbon coating according to the present invention. The complete carbon content amounts to about 20% by weight based on the weight of the coated foil.

This coated foil and—as a reference material—the uncoated foil has been exposed to the so called Blood Chamber Test in order to obtain an in-vitro assessment of the haemocompatible properties.

Six tests on the coated and in parallel on the uncoated material have been performed within a so-called blood chamber. By this method, blood is exposed to the test surface without contact to air. The blood chambers are then incubated at 37 degrees C. Fresh human blood and bovine blood, both anticoagulated with EDTA, is used. In each chamber, 10 ml of blood is exposed to a total surface of 50 $cm^2$, thus a ratio of 0.2 $ml/cm^2$ of blood volume to test material surface area is maintained. After 15 min and after 60 min of blood contact, blood samples are taken from the chambers. In these experiments, parameters of hemolysis (plasma hemoglobin) which is related to blood damage and specific toxity of the test material and of coagulation (partial thromboplastin time=aPTT) were measured. In all experiments, native blood values have also been measured. Plasma hemoglobin, hematocrit and partial thromboplastin time of the fresh blood are measured prior to the contact with the test materials. Thus, it can be observed whether contact to the test material leads to changes of those blood parameters and whether both materials behave differently.

Figure 5:
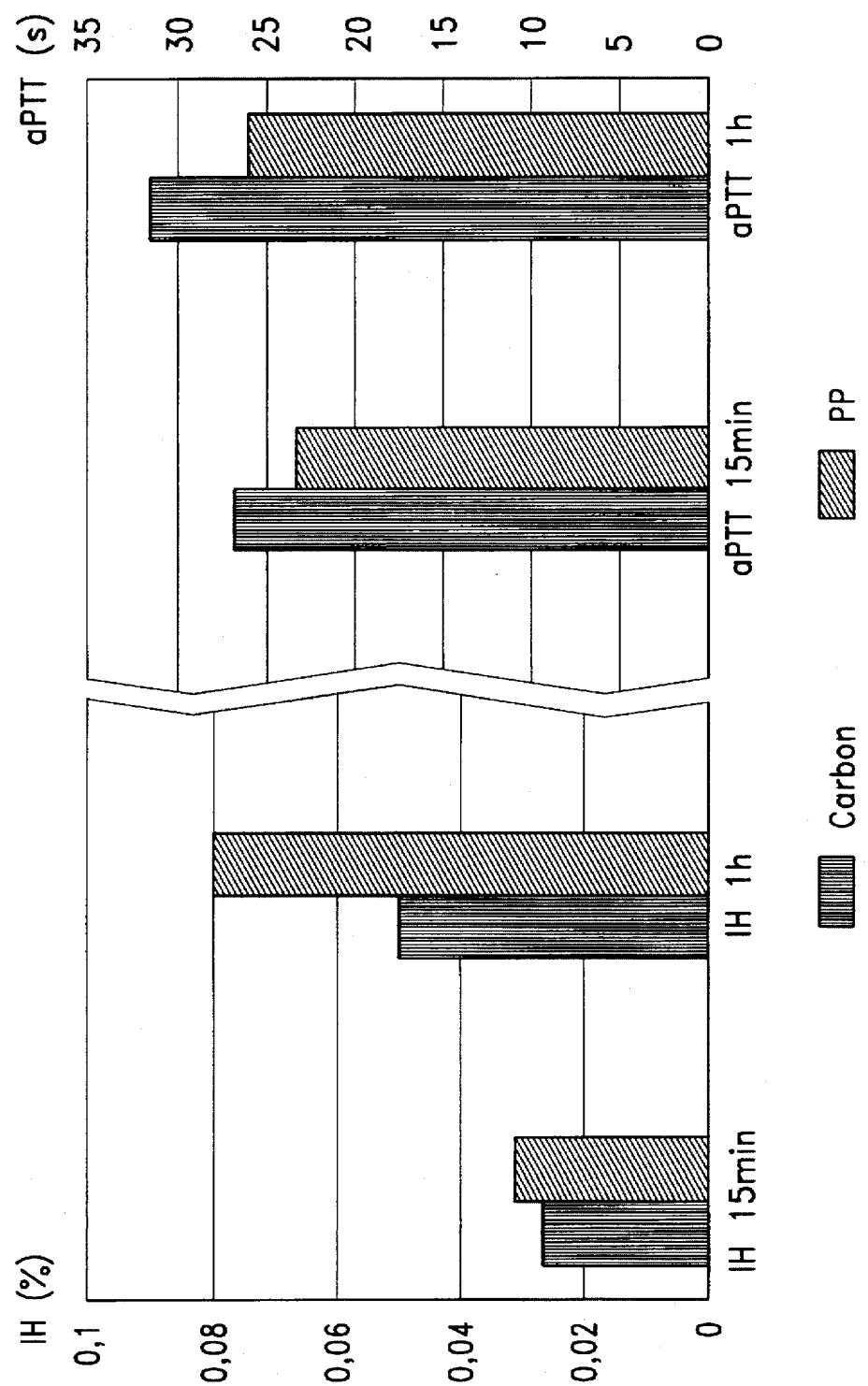
FIG. 5 is a column diagram comparing hemocompatibility related properties to a non-treated polypropylene with a polypropylene coated with a carbon coating according to the present invention.

In FIG. 5, the results of the blood chamber test are shown. For each parameter (IH, aPTT) and blood contact period (15 minutes, 1 hour) the results of the carbon-coated and uncoated polypropylene foil are compared.

The degree of hemolysis is expressed by the index of hemolysis—IH—. Material-induced hemolysis is characterized by the ratio per cent of the amount of free hemoglobin to the total amount of hemoglobin of the blood sample. The amount of free hemoglobin is calculated by the difference of plasma-hemoglobin-concentration before and after test multiplied by the plasma volume. Total hemoglobin is calculated from total hemoglobin concentration multiplied by the whole blood volume. The higher the index of hemolysis, the more the blood has been damaged, ie, more erythrocytes are affected and more hemoglobin has been released. If the values of IH after 15 minutes and 1 hour are compared, an increase in hemolysis with time can be observed, which was also found in earlier experiments, as reported by Glasmacher, B.; Fecke, R.; Zinken, U.; and Wilhelm, K.; in "Material-Induced Hemolysis Research", Report of the Helmholtz-Institut, 1993/1994, Pages 71–81, Aachen, Germany. Hemolysis increases with time and for this reason, test periods of 1 hour should not be exceeded as this effect is not different for different materials. The data in FIG. 5 show that uncoated polypropylene foil exhibits a higher degree of hemolysis than the carbon coated material.

In order to study the effect of carbon coating on coagulation, coagulation times are measured. Partial thromboplastin times (aPTT) were measured first. aPTT is a measure for the intrinsic coagulation system (blood coagulation factors XII, XI, IX, VIII, and with less sensitivity X, V, II, I). aPTT-values of 22 to 35 seconds are normal. In this experiment 28,2 seconds were measured. The aPTT-values after contact with both surfaces are in this range. After 15 minutes as well as after 1 hour blood/material-contact, the carbon coated surface leads to higher times than the PP-surface (cf. FIG. 5). In general, higher clotting times are related to better hemocompatibility.

Figure 3:
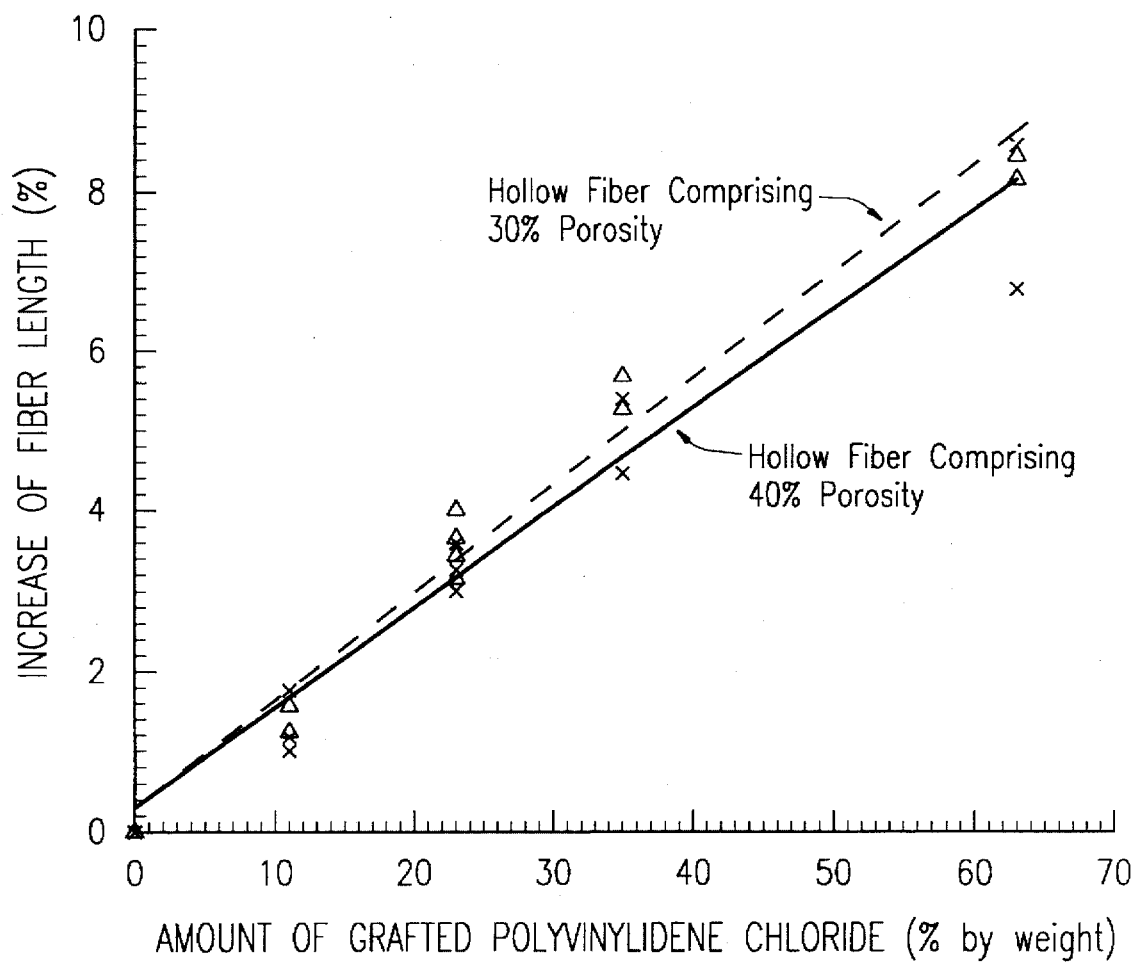
FIG. 3 is a group of fiber length versus amount of grafted polyvinylidene chloride.
Figure 4:
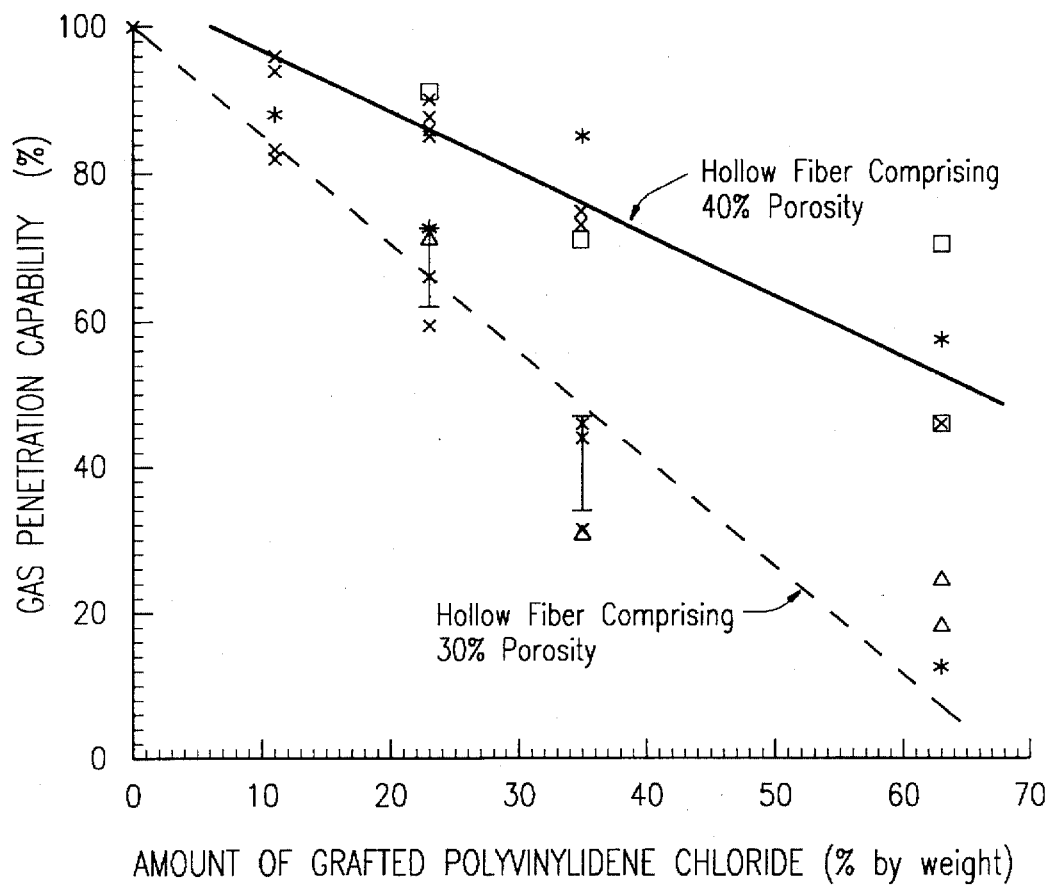
FIG. 4 is a graph of relative gas penetration capability versus amount of grafted polyvinylidene chloride.

The drawings serve for a further explanation of the invention and show along with:

FIG. 1 a graph showing the dependency of the amount of grafted and deposited polyvinylidene chloride (percent by weight based on the weight of the starting fiber having a porosity of 30%) along the ordinate from the duration of the graft-polymerization reaction (minutes) along the abscisse;

FIG. 2 a graph showing the dependency of the amount of grafted and deposited polyvinylidene chloride (percent by weight based on the weight of the starting fiber having a porosity of 40%) along the ordinate from the duration of the graft-polymerization reaction (minutes) along the abscisse;

FIG. 3 a graph showing the increase of the fiber length (percent of the original fiber length) along the ordinate in dependency of the amount of grafted polyvinylidene chloride (percent by weight) along the abscisse for a 30% porosity hollow fiber (interrupted line) and for a 40% porosity hollow fiber (continuous line);

FIG. 4 a graph showing a relative gas penetration capability (a starting porous hollow fiber comprises a gas penetration capability of 100%) along the ordinate in dependency of the amount of grafted polyvinylidene chloride (percent by weight) along the abscisse following either the graft-polimerization step and/or following the dehydrochlorination step for a 30% porosity hollow fiber (interrupted line) and for a 40% porosity hollow fiber (continuous line);

FIG. 5 a column diagram comparing hemocompatability related properties of a non-treated polypropylene foil with a coated polypropylene foil comprising a carbon coating according to the present invention.

Coated yarns as obtained by the before-mentioned non-inventive example (entire polypropylene fiber) have been used to prepare knitted hoses by means of a circular or crosswise knitting machine. The hoses are intended for implantation as vascular grafts comprising an inner diameter of 5 to 12 mm and a length until 600 mm. A part of the hoses have a smooth even wall face. Another part of these hoses have a corrugated structure (so called accordion-like-structure). That hoses comprise a deep black appearance. The coating made of biocompatible carbon material is bound firmly and inseparately to the substrate and may not be scratched off from said substrate. Those hoses have been implantated as vascular grafts, for example in the positions aorto-bifemoral, aorto-iliofemoral, hip-thigh-hollow-of the knee, axillaris-thigh-hollow of the knee, thigh or leg (venous), thigh-tibia.

The main blood circulation within said strucked areas could be rehabilitated with great reliability by means of that artificial vascular grafts. Said vascular grafts provided good tromboresistance and showed a good resistance with respect to infectious inflammation (as far as in the distal areas of the extremeties findings in the form of matter or abscesses have been established from the beginning).

These results of in-vivo experiments are very promising, and confirm that a good biocompatability, especially hemocompatability of the present biocompatible porous hollow fiber is to be expected, too.

A further important aspect of the present invention concerns several kinds of use of the porous hollow fibers having a coating made of a biocompatible carbon material according to the present invention. Typically, the coated hollow fibers have a porosity of about 10 to 50%, especially a porosity of about 20 to about 30%. Those coated porous hollow fibers may be used as exchange materials, diaphragmas and/or semipermeable membranes within devices which will contact blood or plasma outside of the living body (extra corporal blood circulation system). Depending of the specific kind of use, those coated porous hollow fibers may comprise a suited diameter, a suited wall thickness and a suited porosity. Porous hollow fibers which are suited for the graft polymerization reaction and the dehydrochlorination reaction according to the present invention are commercially available. When selecting a specific type of porous hollow fiber, care should be taken that depositing a coating of a biocompatible carbon material according to the present invention may decrease the original porosity in an amount of about 10 to 20%.

According to a preferred embodiment, a coated porous hollow fiber according to the present invention may have an inner diameter of from 100 to 400 μm and an outer diameter of from 250 to 450 μm and may further have a wall thickness of from 20 to 80 μm and may be used for providing exchange materials, diaphragmas and/or semipermeable membranes in oxygenators for providing a gas exchange between two media.

According to another preferred embodiment, a coated porous hollow fiber according to the present invention may have an inner diameter of from 200 to 400 μm and a wall thickness of from 30 to 50 μm and may be used for providing exchange materials, diaphragmas and/or semipermeable membranes in dialyzer apparatuses and dialyzer filter apparatuses.

According to another preferred embodiment, a coated porous hollow fiber according to the present invention may have an inner diameter of from 200 to 400 μm and a wall thickness of from 30 to 60 μm and may be used for providing exchange materials, diaphragmas and/or semipermeable membranes in hemoconcentrator devices.

According to another preferred embodiment, a coated porous hollow fiber according to the present invention may have an inner diameter of from 200 to 400 μm and a wall thickness of from 30 to 60 μm and may be used for providing exchange materials, diaphragmas and/or semipermeable membranes in plasma filter devices.

According to another preferred embodiment, a coated porous hollow fiber according to the present invention may have an inner diameter of from 200 to 400 μm and a wall thickness of from 30 to 60 μm and may be used for providing exchange materials, diaphragmas and/or semipermeable membranes in blood filter devices.

According to another preferred embodiment, a coated porous hollow fiber according to the present invention may have and inner diameter of from 200 to 400 μm and a wall thickness of from 30 to 60 μm and may be used for providing exchange materials, diaphragmas and/or semipermeable membranes as heat exchange fibers in oxygenators.

According to another preferred embodiment, a coated porous hollow fiber according to the present invention may have an inner diameter of from 200 to 400 μm and a wall thickness of from 30 to 60 μm and may be used for providing exchange materials, diaphragmas and/or semipermeable membranes for providing infusion membranes.

Within the fore-mentioned devices, the coated porous hollow fibers may be used in the form of single hollow fibers or in a form of mats or coils prepared from those porous hollow fibers. Commonly, exchange surfaces in a magnitude of about 0.3 to 3.0 m² are required in those devices. In order to provide that magnitude of exchange surfaces, about 6,000 to 400,000 pieces of hollow fibers are required. The use of the coated porous hollow fiber according to the present invention in those devices reduces the requirement for a heparinisation of the blood and reduces any damage of the blood components during a passage of the native blood through those devices.

We claim:

1. A biocompatible porous hollow fiber comprising a substrate made of a polyolefin material, and having a coating of biocompatible carbon material thereon thereby providing a coated porous hollow fiber having a porosity of 10 to 50% and wherein the amount of said carbon material is about 5 to 20% per weight based on the total weight of said hollow fiber and said coating; and wherein said coating is obtained by a process comprising the following steps:

introducing a preformed porous hollow fiber of polyolefin material into an atmosphere of gaseous monomer vinylidene chloride;

inducing a graft-polymerization reaction and grafting a uniform layer of polyvinylidene chloride on the polyolefin material forming said porous hollow fiber; and substantially eliminating and removing hydrogen chloride from said polyvinylidene chloride in order to convert said layer of polyvinylidene chloride into a coating of biocompatible carbon material.

2. A biocompatible porous hollow fiber according to claim 1, wherein said coating of biocompatible carbon material being chemically bound to the polyolefin material forming the porous hollow fiber.

3. A biocompatible porous hollow fiber according to claim 1, wherein said coating of biocompatible carbon material is covalently bound to the polyolefin material forming the porous hollow fiber.

4. A biocompatible porous hollow fiber according to claim 1, wherein said coating of biocompatible carbon material has a residual chlorine content of less than 6% based on the chlorine content of the original layer of polyvinylidene chloride.

5. A biocompatible porous hollow fiber according to claim 1, wherein said graft polymerization is a gas phase graft polymerization induced by means of an ionizing radiation.

6. A biocompatible porous hollow fiber according to claim 5, wherein said ionizing radiation is gamma radiation.

7. A biocompatible porous hollow fiber according to claim 1, which comprises inducing said graft polymerization reaction by means of an ionizing radiation having an average dose rate of from about 0.1 to about 1.5 watt per kg radiated material.

8. A biocompatible porous hollow fiber according to claim 1, wherein 0.1 to 1.2 parts per weight of polyvinylidene chloride have been grafted per 1 part per weight of polyolefin material of said porous hollow fiber.

9. A biocompatible porous hollow fiber according to claim 1, wherein 0.4 to 0.6 parts per weight of polyvinylidene chloride have been grafted per 1 part per weight of polyolefin material of said porous hollow fiber.

10. A biocompatible porous hollow fiber according to claim 1, wherein the substantially eliminating and removing hydrogen chloride has been effected by treatment with a hot concentrated aqueous ammonia solution.

11. A biocompatible porous hollow fiber according to claim 1, wherein the porous hollow fiber is consisting of a polypropylene material;

wherein the coating comprises a carbon material having a density of approximately 1.8 g/cm³.

12. A biocompatible porous hollow fiber according to claim 1, wherein said polyolefin is polypropylene.

13. A biocompatible porous hollow fiber according to claim 1, wherein said coating of biocompatible carbon material has a residual chlorine content less than 3% based on the chlorine content of the original layer of polyvinylidene chloride.

14. A biocompatible porous hollow fiber according to claim 1, wherein said substantially eliminating and removing hydrogen chloride is carried out at a temperature of from 80° C. to 100° C.

15. A biocompatible porous hollow fiber according to claim 10, wherein said substantially eliminating and removing hydrogen chloride continues for a duration of at least 20 hours.

16. A biocompatible porous hollow fiber according to claim 1, wherein the coating has a thickness of more than 5 microns.

17. A biocompatible porous hollow fiber according to claim 1, wherein said layer of polyvinylidene chloride is an epitaxial layer.

18. A biocompatible porous hollow fiber according to claim 1 wherein the porous hollow fiber has a porosity of 20 to 40%.

19. The biocompatible porous hollow fiber of claim 1, wherein said substantially eliminating and removing hydrogen chloride comprises treating with a hot aqueous ammonia solution comprising an ammonia concentration of 20 to 35% by weight.

20. The biocompatible porous hollow fiber of claim 1, which further comprises after said substantially eliminating and removing hydrogen chloride, rinsing said substrate with hot water.

21. The biocompatible porous hollow fiber of claim 20, which further comprises after said rinsing, heating said substrate under reduced pressure.

22. The biocompatible porous hollow fiber of claim 1, wherein said preformed porous hollow fiber has pores with dimensions less than 1 micron.

23. The biocompatible porous hollow fiber of claim 1, wherein said polyolefin is a copolymer of propylene with another $\alpha$-olefin.

* * * * *